(12) United States Patent
Blake, III (10) Patent No.: US 6,423,079 B1
(45) Date of Patent: Jul. 23, 2002

(54) REPEATING MULTI-CLIP APPLIER (76) Inventor: Joseph W Blake, III, 77 Locust St., New Canaan, CT (US) 06840

( * ) Notice: Subject to any disclaimer, the term of this patent is extended or adjusted under 35 U.S.C. 154(b) by 0 days.

(21) Appl. No.: 09/521,444

(22) Filed: Mar. 7, 2000

(51) Int. Cl.[7] .............................................. A61B 17/04
(52) U.S. Cl. ...................................................... 606/143
(58) Field of Search ................................. 606/242, 243

(56) References Cited

U.S. PATENT DOCUMENTS

| | | | | | |
|---|---|---|---|---|---|
| 4,425,915 A | * | 1/1984 | Ivanov | ........................ | 606/243 |
| 4,430,997 A | * | 2/1984 | DiGiovanni et al. | ........ | 606/243 |
| 5,084,057 A | * | 1/1992 | Green et al. | ................. | 606/243 |
| 5,104,395 A | * | 4/1992 | Thornton et al. | ........... | 606/243 |
| 5,431,668 A | * | 7/1995 | Burbank, III et al. | ...... | 606/243 |
| 5,527,318 A | * | 6/1996 | McCarry | .................... | 606/243 |

\* cited by examiner

*Primary Examiner*—Gary Jackson
(74) *Attorney, Agent, or Firm*—Patrick J. Walsh (57) ABSTRACT

A repeating multi-clip applier for surgery with scissor-type or pistol grip operating handles, and a clip feeding and applying mechanism actuated by linear reciprocating movement generated by the handles. A unitary linear actuating rod and clip supply channel together with clip feed mechanisms reciprocate rearward-to-forward as the handles move for applying a clip in surgery and for advancing clips into the applying jaws.

17 Claims, 5 Drawing Sheets

REPEATING MULTI-CLIP APPLIER

BACKGROUND OF THE INVENTION

The present invention relates to an appliance for affixing surgical or ligating clips and more particularly to an appliance for rapidly employing several clips at a surgical site. There are many different designs for surgical clip applicators for a variety of surgical procedures including laproscopy in which a clipping appliance fits through a trocar tube into a body cavity where the clips are applied.

This invention provides a repeating multi-clip applier having a simplified mechanism for applying clips which mechanism is suitable for the full spectrum of clip appliers including laparoscopy. The applier mechanism is particularly adaptable to the disposable cartridge/fixed handle design. The simplified mechanism reduces tooling and assembly requirements, provides high operating reliability at lower product cost.

SUMMARY OF THE INVENTION

A surgical clip applicator according to the invention comprises an operating handle and clip applying mechanism having an operating cycle in which operating levers are squeezed together and released. In this cycle, a clip is applied in surgery and the clip applicator is reloaded from a clip supply channel for clip application in the next cycle.

The applicator provides a moveable clip supply channel containing a line of clips that are released seriatim. The supply channel integrates a clip pusher and an escapement or clip stop spring in a single stamped unit.

Clip crimping jaws apply a clip with a rearward movement of a camming member thereby allowing the functions of clip loading and jaw closure to be coordinated and operated by a single sliding bar moving reciprocally to load and fire clips.

A preferred embodiment of the clip actuating mechanism includes a combined actuating rod and in-line clip supply channel together with clip indexing mechanisms arranged so that with a squeeze of the operating levers, the actuating rod moves rearward in the appliance to apply a clip in surgery, capture the next in-line clip, indexes a line of clips rearward away from the clip jaws, and that with release of the operating levers, the jaws open, the next in-line clip is loaded into the jaws, the second next in-line clip is separated from the line, and the clip indexing movement is reset for the next cycle.

The clip applicator provides a novel mechanism with minimal complexity especially suited to disposable cartridge for fixed handle appliances.

A clip applicator according to the invention employs low operating force without recoil, a clip counter, jaw lockout after the last clip and is adaptable for use as a quick snap-in disposable cartridge with a fixed non-disposable operating handle. An operating handle that provides linear reciprocating motion including scissors-type or pistol grip may be used in the invention.

OBJECTS OF THE INVENTION

An object of the invention is to provide a novel clip applicator with minimum complexity and with adaptability to a complete range of clip applicators including laproscopic use.

Another object of the invention is to provide a clip applicator adaptable for use with a replaceable cartridge.

Another object of the invention is to provide a clip applicator in which clip feed and applying mechanisms are driven by an actuator having a linear reciprocating motion generated by operating handles.

Another object of the invention is to provide a surgical clip applier useful with a variety of operating handle designs.

Other and further objects of the invention will become apparent with an understanding of the following detailed description of the invention or upon employment of the invention in practice.

A preferred embodiment of the invention has been chosen for detailed description to enable those having ordinary skill in the art to which the invention appertains to readily understand how to construct and use the invention and is shown in the accompanying drawing in which.

DETAILED DESCRIPTION OF THE PREFERRED EMBODIMENT

Referring to the drawing, a preferred embodiment of the repeating multi-clip applier 10 comprises handle 12 and clip applicator 14.

The handle 12 (FIG. 2) includes a central casing 16 formed of upper 16a and lower 16b shells each having aligned confronting journal pin guiding slots 16c. The shells are joined to each other along edges 16d to define an enclosure 16e for receiving handle components 18 including actuating levers 18a–b pivotally mounted on adjacent posts 18c–d, links 18e–f joined to each other by journal pin 18g and connected by pivot pins 18h–i to levers 18a–b, and compression spring 20.

Figure 2:
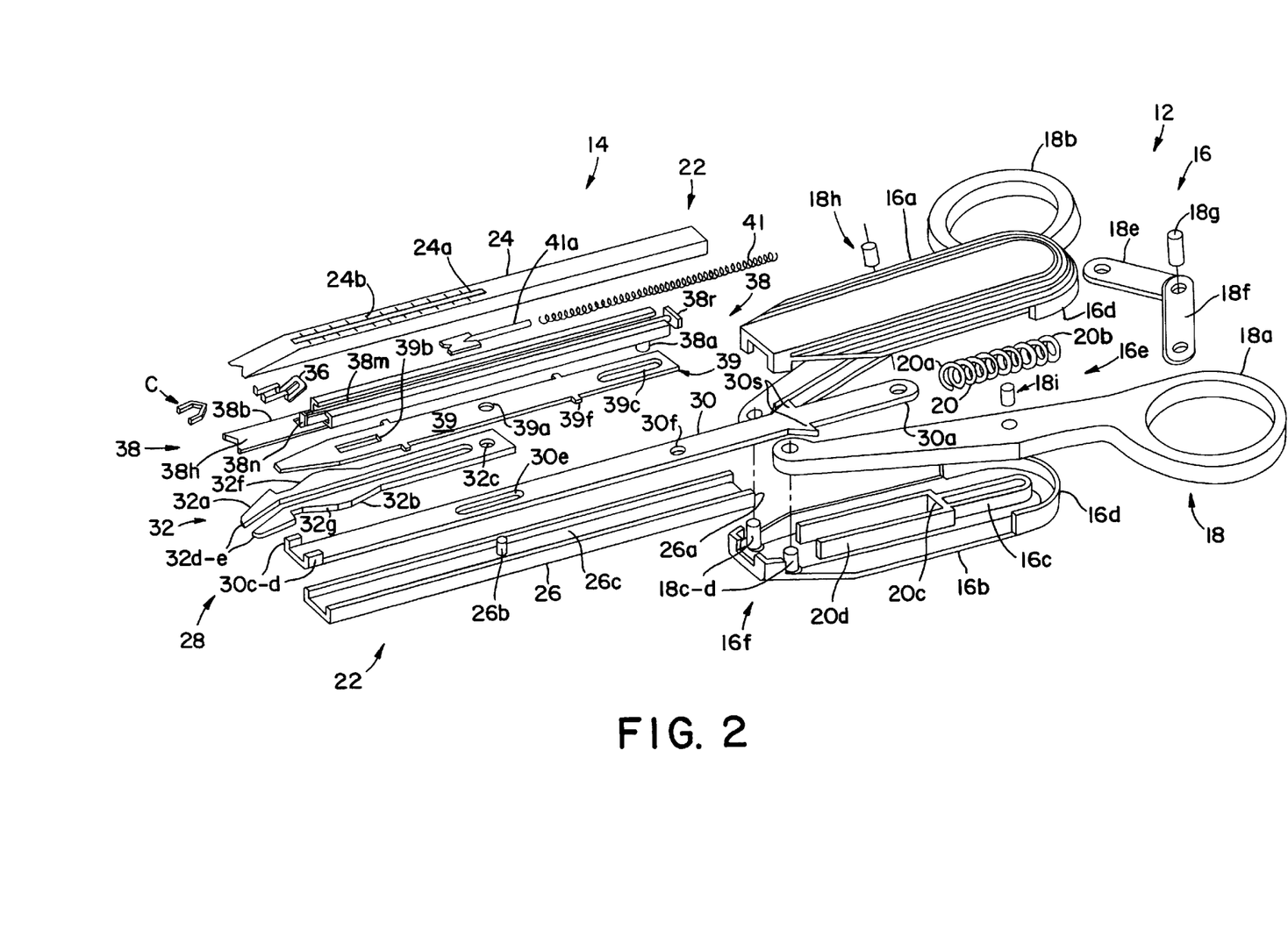
FIG. 2 is an exploded perspective view of the components of a preferred embodiment of surgical clip applicator.

In assembly, the compression spring is mounted on actuating rod 30 with one spring end 20a abutting rod shoulders 30s and the other spring end 20b abutting a rear face 20c of a spring housing 20d. The end 30a of the actuating rod extends through the spring for connection to links 18e–f by means of journal pin 18g. The exposed ends of the journal pin fit into the guiding slots 16c which define the axial excursion of the actuating rod. When assembled, the spring urges the actuating rod forward in a straight line and (by means of actuating rod connection at 30a to the journal pin 18g and links 18e–f) urges the actuating levers 18a–b to pivot outward from the casing to normal position. In use, the levers with finger loops are moved together (inward) against the spring for the purpose of applying a clip and moved apart (outward) to reload the applicator jaws with a clip.

It is to be understood that the links-actuating rod journal pin 18g moves in a rearward then forward linear excursion within the guiding slots for each inward-to-outward cycle of the operating levers. This reciprocating linear motion serves to operate the clip applicator 14 by means of the actuating rod 30.

In practice the clip applicator 14 can be used with any suitable handle that provides linear reciprocating motion. The description of a scissors-type handle is illustrative.

The clip applicator 14 comprises an applicator housing 22 including cover 24 and base 26 connected to the forward end 16f of the handle casing with the applicator housing enclosing and forming part of a clip applicator mechanism 28. In the following description, the applicator housing cover and base are regarded as stationary in relation to movement of the applicator mechanism components.

The applicator housing base 26 is an elongate open ended channel secured at its rear end 26a to the operating handle casing and having an anchor pin 26b affixed to the channel base 26c.

The elongate actuating rod 30 is located in the applicator base channel 26c with the rod connected at its rear end 30a to the handle link journal 18g for receiving linear reciprocating motion with respect to the stationary base channel 26c for each cycle of the handle operating levers. The actuating rod at its front end includes upstanding cooperating cam members 30c–d for closing and opening clip applicator jaws 32. The actuating rod also includes an anchor pin slot 30e to accommodate reciprocal movement of the rod in the base channel and a circular hole 30f to receive a retaining pin 38a fitted to the clip supply channel as described below.

Clip applying jaws 32 comprising spring biased arms 32a–b (FIGS. 2, 4a–b) are mounted at hole 32c to anchor pin 26b on the applicator base with the jaws 32d–e projecting from the front end of the channel.

The applicator jaws are affixed to the base channel so that as the actuator rod reciprocates, cam means 30c–d (FIGS. 2, 4a–b) forming part of the actuating rod ride along cam surfaces 32f–g of the applicator jaws for closing the jaws to apply a clip and for opening the jaws to receive another clip. The normal position for the actuating rod and jaws occurs with the actuating rod at the forward end of linear excursion, with the jaws open and with the actuating rod cam means in an inactive position with respect to applicator jaws.

Preferred and modified applicator jaws are illustrated in FIGS. 4a–b and 5a–b.

Figure 4A:
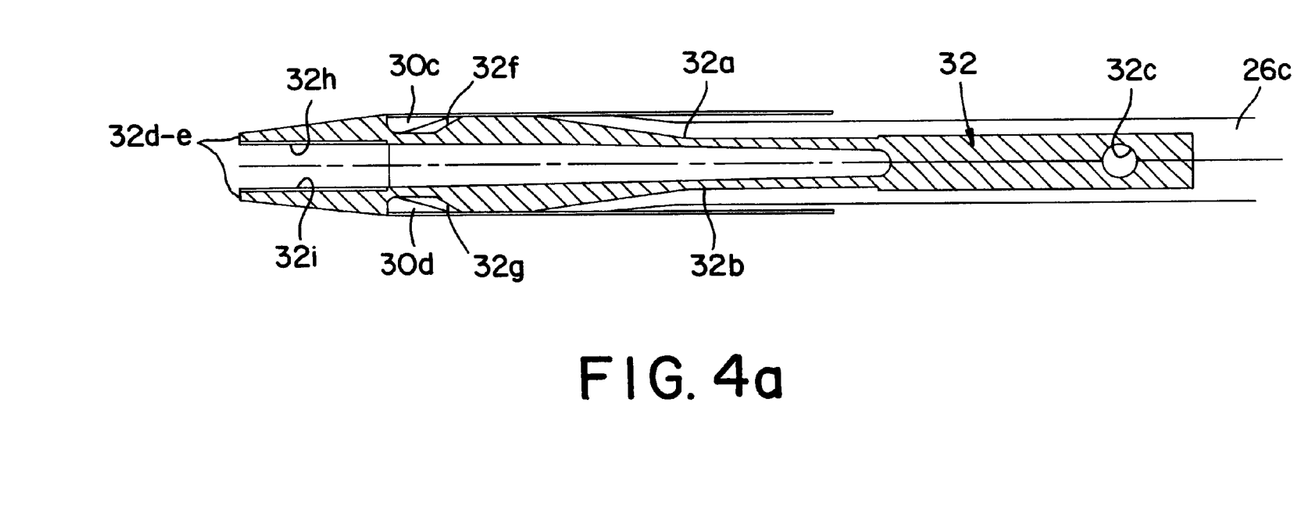
FIGS. 4a–4b are sequential plan views of a preferred embodiment clip applicator jaws in open and closed positions, respectively.
Figure 4B:
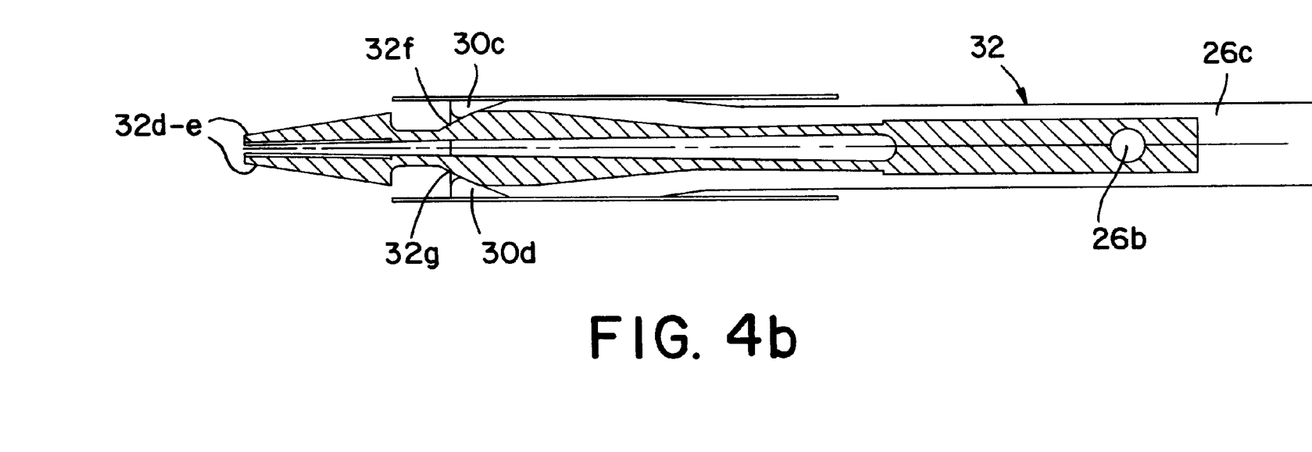

FIGS. 4a–b illustrate spring biased applicator jaws 32 affixed at a rear point 32c to the applicator housing anchor pin 26b with spring biased arms able to move from open-to-closed-to-open positions in applying a clip. The inner surfaces 32h–i of the jaws are recessed to form cooperating channels for movement of each clip into the jaws. The outer surfaces of the jaws have aligned recesses 32f–g defining cam surfaces cooperating with aligned cam members 30c–d affixed to the actuating rod 30 for the purpose of closing the jaws for each rearward excursion of the actuating rod (FIG. 4b). The jaws are released to spring open on the forward excursion of the actuating rod placing the cam members within the recesses (FIG. 4a).

Figure 5A:
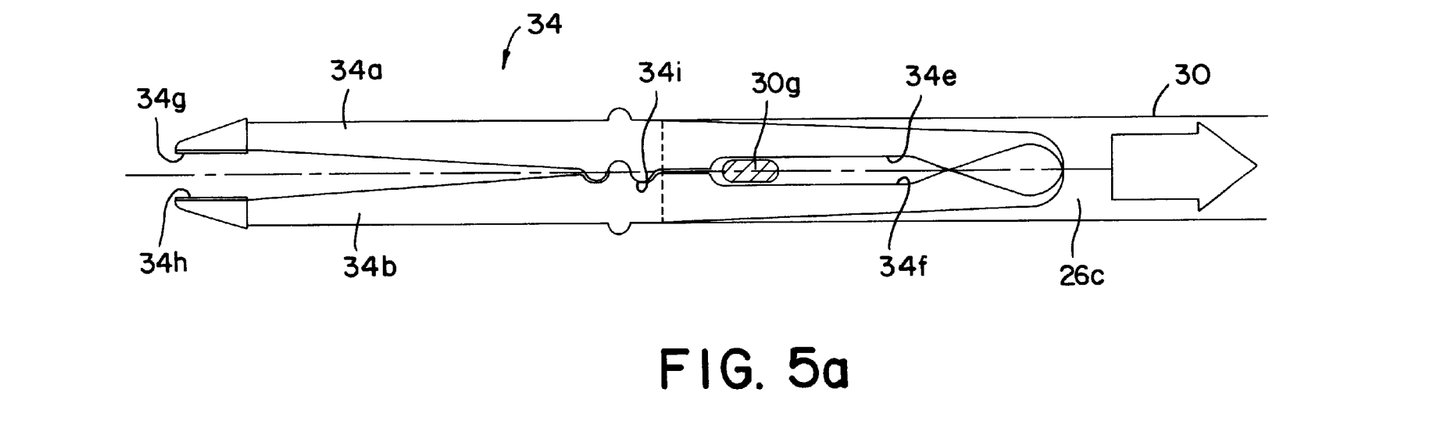
FIGS. 5a–5b are sequential plan views of a modified embodiment clip applicator jaws in open and closed positions, respectively.
Figure 5B:
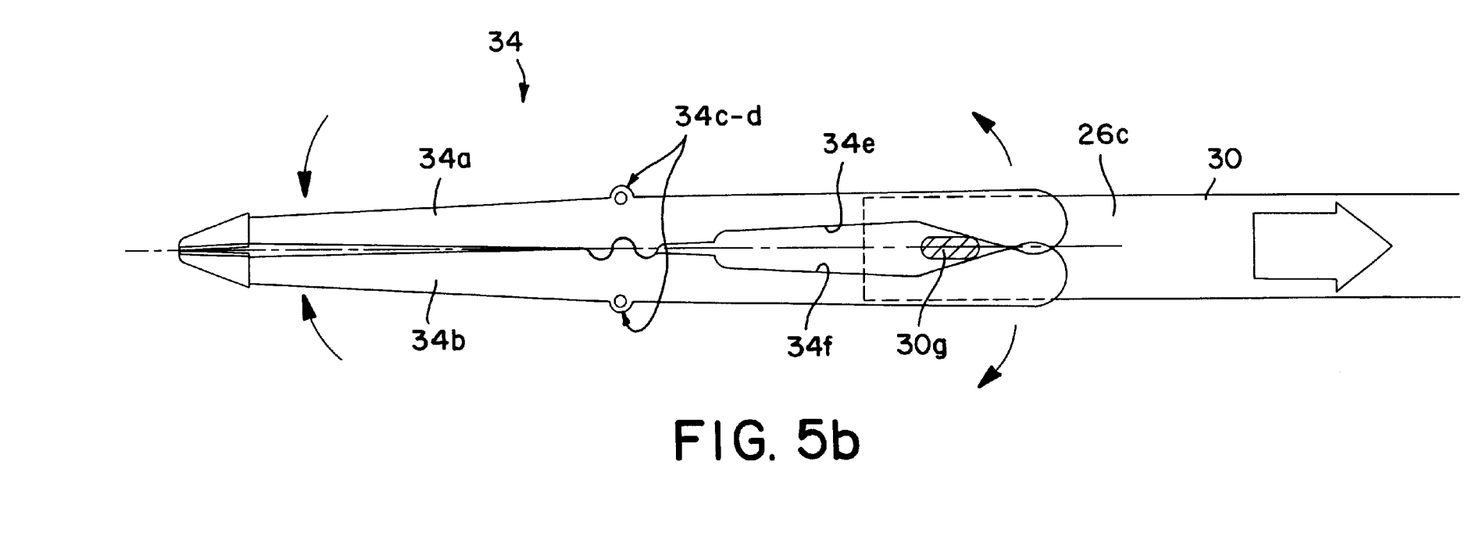

FIGS. 5a–b illustrate pivoted applicator jaws 34 with pivot arms 34a–b affixed at aligned central pivot points 34c–d to the applicator housing base 26c. The rearward inner surfaces of the jaws have aligned recesses defining cam surfaces 34e–f cooperating with cam member 30g affixed to the actuating rod 30 for the purpose of closing the jaws for each rearward excursion of the actuating rod (FIG. 5b). The jaw arms move from open-to-closed-to-open positions in applying a clip. The jaws are moved to normally open position by means of a spring (not shown) or by a positive displacement cam means. The forward inner surfaces 34g–h of the jaws are recessed to form cooperating channels for holding each clip in the jaws as the jaws close.

The jaws move open on the forward excursion of the actuating rod and cam member 30g (FIG. 5a). A sinuous interface 34i of the jaw arms ensures true rocking or pivoting movement of the jaw arms from open to closed positions.

The applicator mechanism 28 also includes a clip supply channel 38 (FIGS. 2, 3a–c) which is affixed to and reciprocates with the actuating rod 30 by means of an anchor pin 38a at the underside the channel which fits into hole 30f in the actuating rod. The supply channel 38 includes an elongate base plate 38b with upstanding sides 38c to define a central channel 38d and includes flanges 38e defining inwardly directed side channels 38f–g for receiving and retaining a line of clips C. The clip supply channel has an integral forwardly extending pusher plate 38h preferably with notched front edge conforming to clip contour for the purpose of pushing each clip into the jaws as it leaves the supply channel. A clip stop spring 38m with vertical tip 38n is formed integral in the base plate 38b for gripping the leading clip $C_L$ at midpoint. The clip stop spring has a "spring set" wherein the spring is normally positioned or biased below the surface of base plate 38c with the spring being accommodated in a slotted cam plate 39 located underneath the channel.

The cam plate 39 (FIG. 2) is fixed to the stationary housing by means of tabs 39t or mounted at hole 39a to anchor pin 26b, so that the back edge of the slot 39b acts as a cam to urge the clip stop spring and its tip 38n upward into the path of clips C when the clip cartridge 38 moves rearward with the actuating rod 30. A slot 39c in the cam plate accommodates reciprocal movement of the clip cartridge/actuating rod connecting pin 38a.

The housing cover 24 has an elongate transparent slot 24a (FIG. 1) through which a user can see the supply of clips. The cover may also have count marks 24b indicating the number of clips remaining in the applicator. The cover (FIGS. 3a–c) also has on its inner surface a clip block 24c, a clip capture spring 36 and a guide ramp 24d for positioning clips for movement into clip applying jaws as more fully described below. The underside surface of the cover may also have a set of longitudinally extending ratchet teeth 24e (FIG. 3b) forming a part of a clip advancing mechanism described below.

A clip advancing mechanism 40 (FIG. 3b) is positioned and retained in the clip supply channel 38d and side channels 38f–g in engagement with the last clip $C_Z$ for advancing the line of clips along the supply channel. The clip advancing mechanism includes a clip follower 40a with forwardly directed fingers 40b–c for engaging clip shoulders for constantly maintaining a force on the line of clips, a sinuous compression spring 40d, and a ratchet head 40e. The ratchet head is provided with upper 40f and lower 40g tangs or spring biased ratchet pawls for engagement, respectively, with ratchet edges or teeth 24e in the under side of the housing cover and ratchet openings 38p in the supply channel base plate 38b.

Figures 3A, 3B, 3C:
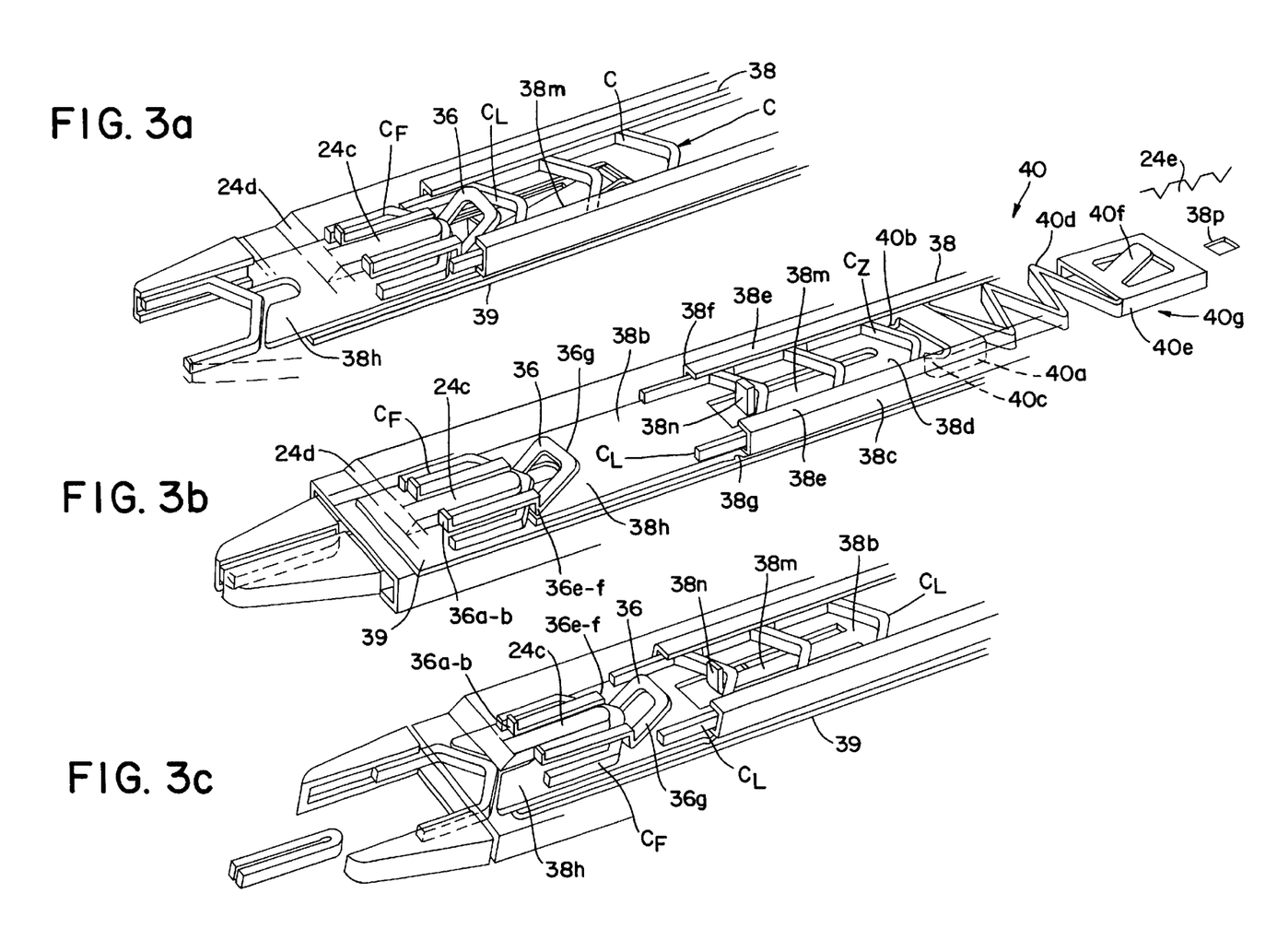
FIGS. 3a–3c are sequential fragmentary perspective views of a surgical clip applicating mechanism according to the invention.

The ratchet head, the clip follower and follower spring by their design and operation, and in cooperation with the movable clip stop spring 38m, regulate step-by-step or indexing movement of a line of clips through the supply channel toward the applicator jaws.

In normal (or forward) position of the actuating rod 30 and supply channel 38 (which are affixed to each other), the bias spring 40d, clip follower 40a and ratchet head 40e maintain contact and force on the clip line urging the line toward the clip stop spring 38m by means of upper pawl 40f engagement with ratchet teeth 24e in the housing cover and by means of lower pawl 40g engagement with ratchet openings 38p in the supply channel base plate while the clips are at rest in the supply channel.

The clip advance mechanism, the bias spring and clip follower, the cover ratchet teeth, the base plate ratchet openings, and the clip stop spring act together for step-by-step or indexed movement of the clips down the supply channel as now described.

With the actuating rod and supply channel in forward or normal position, the upper pawl and compression spring hold the clip line stationary against the clip stop spring 38m. When the actuating rod 30 and supply channel 38 move rearward with squeeze of the operating levers, the ratchet head and upper pawl remain stationary while the compression spring accommodates rearward movement of the clip stop spring and the contiguous line of clips. The rearwardly moving supply channel slips over the lower pawl 40g bringing the next forward ratchet opening 38p into contact with the lower pawl thereby indexing forward by one step the relative position of the ratchet head and the supply channel.

Next the actuating rod and supply channel and line of clips move forward as a unit into normal position. During this forward movement, the upper pawl 40f slips one notch along the under side of the housing cover into engagement with the next ratchet tooth 24e.

In lieu of the clip advancing mechanism 40, an elongate compression spring 41 (FIG. 2) may be employed for advancing clips in the clip supply channel. As shown, a compression spring attached to a channel back wall 38r and to a spring head 41a lies in the clip channel for engaging and moving a line of clips C in the channel by spring force.

Referring to FIGS. 3a–c, with forward movement of the supply channel and coherent line of clips, a first in line of clips $C_F$ comes to rest against the clip block 24c. The capture spring 36 straddles the clip block and separates clip $C_F$. The capture spring 36 is stationary in that it is affixed to the under side of the housing cover in position to capture and hold the lead clip at the end of the forward excursion of the actuating rod and supply channel. The capture spring takes and separates the lead clip from the clip line in preparation for movement of the lead clip into the applicator jaws on a subsequent applicator cycle.

The capture spring in preferred form is generally U-shaped with front tabs 36a–b affixed to the cover, with spaced shoulders 36e–f, and with inclined rear end 36g. The spring captures clip $C_F$ by reaction as the inclined end rides up on forwardly moving clip $C_F$ and snaps down as the clip passes the shoulders. Such clip capture occurs as the actuating rod and supply channel reciprocate during operation of the applicator, as detailed below.

At the end of rearward excursion of the supply channel (FIG. 3b), the capture spring 36 pushes clip $C_F$ downward and out of engagement with the clip block 24c and into the path of the pusher plate 38h. The pusher plate then engages the rear of captured clip $C_F$ with its contoured edge to advance clip $C_F$ into the applicator jaws on forward movement of actuating rod and supply channel. The guide ramp 24d on the cover guides clip $C_F$ into the jaws.

Figure 1:
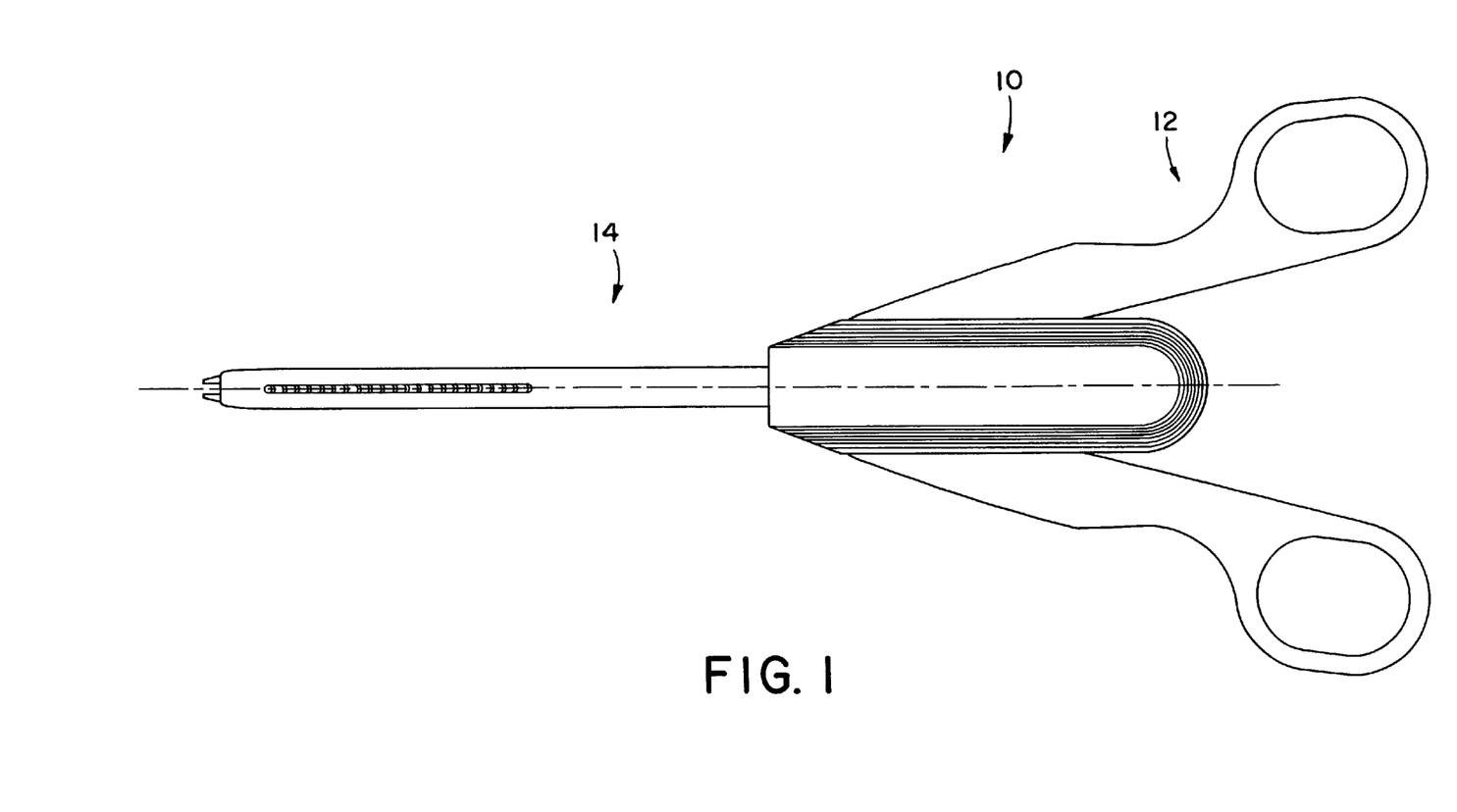
FIG. 1 is a plan view of a surgical clip applicator according to the invention.

The operation of the applicator is as follows. Referring to FIGS. 1, 3a and 4a, the housing cover and base are stationary with respect to movements of the component parts of the actuating mechanism. At the beginning of an operating cycle (or normal position), the handle actuating levers are positioned apart, the actuating rod and supply channel are in forward position, the jaws are open holding a clip in position for surgical application, jaw actuating cam means are in inactive position, the lead clip in the capture position, the pusher plate lies under the lead clip, the clip stop spring is inactive and lies in the cam plate recess below the surface of the pusher plate, and the clip follower engages the last in line clip, the spring biased line of clips is in contact with lead clip $C_F$, the lower pawl engages a corresponding supply channel ratchet edge, and the upper pawl engages a cover ratchet tooth.

By squeezing the handle levers together (FIGS. 3b and 4b), the actuating rod and supply channel move rearward relative to the stationary cover and base to accomplish:

a. retraction of the actuating rod cam means along the jaws cam surfaces to close the jaws and apply a clip;

b. movement of the pusher plate relative to the cam plate whereby the stop spring is cammed up so its tip grips the next in line clip $C_L$ and by rearward movement the stop spring separates the clip stack from the lead clip $C_F$;

c. the captured clip $C_F$ is held in place under the capture spring;

d. movement of the pusher plate from underneath into position behind the captured clip $C_F$;

e. the upper pawl of the ratchet head is in engagement with a ratchet tooth of the housing cover as the clip follower and follower spring maintain back pressure on the clip line in the supply channel thereby holding the ratchet head stationary with respect to the upper housing cover as the staple supply channel moves rearward with the actuating rod, f. indexing the lower pawl one step of relative movement between the ratchet head and the supply channel;

and by releasing the handle levers to move apart, the actuating rod and supply channel move forward in relative movement to the stationary cover and base to accomplish:

g. movement of the pusher plate to advance the captured clip $C_F$ into the jaws;

h. movement of the actuating rod cam means along the jaws cam surfaces into inactive position opening the jaws;

i. with the lower pawl in engagement with a ratchet edge of the supply channel advance the ratchet head and the clip line and the supply channel for moving the clip line and the lead clip $C_L$ toward capture position;

j. indexing the upper pawl one step along the cover ratchet teeth; and k. the pusher plate and stop spring moving relative to the cam plate with the stop spring reentering is slot in the cam plate out of the path of the clip line so as to permit the next in line clip $C_L$ to advance along the surface of the pusher plate to deflect the capture spring and be captured as $C_F$.

The invention provides that the clip applicator of FIG. 2 of the drawing can be made as a disposable cartridge to be inserted into a non-disposable handle with the cartridge removed from the handle and discarded after its clips are consumed. In a cartridge arrangement both the cartridge housing and rear end of the actuating rod have plug-in connections to the handle housing and link journal respectively.

Various changes may be made to the structure embodying the principles of the invention. The foregoing embodiments are set forth in an illustrative and not in a limiting sense. The scope of the invention is defined by the claims appended hereto.

I claim:

1. A repeating surgical clip applier comprising a handle having means for providing linear reciprocating motion of rearward and forward strokes, a clip applicator affixed to the handle in position to receive the reciprocating motion, the clip applicator having a stationary housing including a base and cover, the housing base being an elongate channel having an open end, clip applying jaws mounted at the open end of the base, the jaws being adapted to close in applying a clip and to open for receiving a clip, actuator means supported by the housing base for receiving rearward and forward strokes from the handle, the actuator means for closing and opening the jaws, a clip channel for supplying a line of clips, the clip channel being affixed to the actuator means for reciprocating motion therewith, means for urging a line of clips through the supply channel, means for capturing the lead clip from the supply channel in response to motion of the actuator means and supply channel, and means for moving the lead clip into the applicator jaws.

2. A repeating surgical clip applier as defined in claim 1 in which a compression spring is the means for urging a line of clips through the supply channel.

3. A repeating surgical clip applier as defined in claim 1 in which a compression spring and indexing means are the means for urging a line of clips through the supply channel.

4. A repeating multi-clip applier as defined in claim 1 in which the means for moving the lead clip into the applicator jaws is a pusher plate integral with the clip channel.

5. A disposable surgical clip cartridge for use with manual operating means which provides the cartridge with linear reciprocating motion defined by a rearward to forward excursion, the cartridge comprising a housing including a cover and base, the base being an elongate open ended channel and adapted for connection at one of its ends to the manual operating means, clip applying jaws fitted to and extending from the other end of the base, the cover mounted to the base and together with the base defining stationary means for enclosing a clip actuating mechanism, a clip actuating means located within the housing and including means for receiving reciprocating motion from the manual operating means, a clip supply channel for carrying a line of clips for application in surgery, the clip supply channel linked to the means for receiving reciprocating motion, means for advancing the line of clips along the supply channel, means for separating a clip from the line of clips for each rearward to forward excursion of the means receiving reciprocating motion, means to move a clip into the jaws for each rearward to forward excursion of the means receiving reciprocating motion, means for closing the jaws to apply a clip and means to reopen the jaws for each rearward to forward excursion of the means receiving reciprocating motion.

6. A disposable surgical clip cartridge as defined in claim 5 in which a compression spring is the means for urging a line of clips through the supply channel.

7. A disposable surgical clip cartridge as defined in claim 5 in which a compression spring and indexing means are the means for urging a line of clips through the supply channel.

8. A repeating surgical clip applier comprising a handle having means for providing linear reciprocating motion of rearward and forward strokes, a clip applicator affixed to the handle in position to receive the reciprocating motion, the clip applicator having a stationary housing including a base and cover, the housing base being an elongate channel having an open end, clip applying jaws mounted at the open end of the base, the jaws being adapted to close in applying a clip and to open for receiving a clip, actuator means supported by the housing base for receiving rearward and forward strokes from the handle, the actuator means for closing and opening the jaws, a clip channel for supplying a line of clips, the clip channel being affixed to the actuator means for reciprocating motion therewith, means for indexing line of clips advance through the supply channel in response to rearward and forward motion of the actuator means and supply channel, means for capturing the lead clip from the supply channel in response to motion of the actuator means and supply channel, and means for moving the lead clip into the applicator jaws.

9. An applicator for surgical clips comprising a handle and an applicator mechanism, the handle providing rearward and forward linear motion to the applicator, the applicator mechanism having jaws for applying clips in surgery, a clip supply channel, a clip advancing mechanism for step by step movement of the clips through the supply channel in response to rearward and forward movement provided by the handle, means for applying a staple in surgery in response to rearward movement, and means for loading a clip into the jaws in response to forward movement.

10. A disposable surgical clip cartridge for use with manual operating means which provides the cartridge with linear reciprocating motion defined by a rearward to forward excursion, the cartridge comprising a housing including a cover and base, the base being an elongate open ended channel and adapted for connection at one of its ends to the manual operating means, clip applying jaws fitted to and extending from the other end of the base, the cover mounted to the base and together with the base defining stationary means for enclosing a clip actuating mechanism, the cover having first clip indexing means, a clip actuating means located within the housing and including means for receiving reciprocating motion from the manual operating means, a clip supply channel for carrying a line of clips for application in surgery, the clip supply channel linked to the means for receiving reciprocating motion, the supply channel having second clip indexing means, means cooperating with the clip supply channel and with the first and second clip indexing means to advance the line of clips one step along the supply channel for each rearward to forward excursion of the means receiving reciprocating motion, means for separating a clip from the line of clips for each rearward to forward excursion of the means receiving reciprocating motion, means to move a clip into the jaws for each rearward to forward excursion of the means receiving reciprocating motion, means for closing the jaws to apply a clip and means to reopen the jaws for each rearward to forward excursion of the means receiving reciprocating motion.

11. A surgical clip applicator comprising manual operating means to provide reciprocating motion defined by a linear rearward to forward excursion for each cycle of the manual means, a stationary housing including a cover and base, the base being an elongate open ended channel connected at one of its ends to the manual operating means, clip applying jaws fitted to and extending from the other end of the base, the cover mounted to the base and together with the base defining stationary means for enclosing a clip actuating mechanism, the cover having first clip indexing means, a clip actuating means located within the housing and including an actuating rod for receiving reciprocating motion from the manual operating means, a clip supply channel for carrying a line of clips for application in surgery, the clip supply channel linked to the actuating rod for movement through rearward to forward excursion, the supply channel having second clip indexing means, the clip supply channel having a movable clip stop, means cooperating with the clip supply channel, with the first and second clip indexing means, and with the clip stop to advance the line of clips one step along the supply channel for each rearward to forward excursion of the actuating rod, means for separating a clip from the line of clips for each rearward to forward excursion of the actuating rod, means to move a clip into the jaws for each rearward to forward excursion of the actuating rod, and means for closing the jaws to apply a clip and to reopen the jaws for each rearward to forward excursion of the actuating rod.

12. A surgical clip applicator comprising manual operating means to provide reciprocating motion defined by a linear rearward to forward excursion for each cycle of the manual means, a stationary housing including a cover and base, the base being an elongate open ended channel connected at one of its ends to the manual operating means, clip applying jaws fitted to and extending from the other end of the base, the cover mounted to the base and together with the base defining stationary means for enclosing a clip actuating mechanism, the cover having a ratchet tooth surface forming part of clip indexing means, a clip actuating means located within the housing and including an actuating rod for receiving reciprocating motion from the manual operating means, a clip supply channel for carrying a line of clips for application in surgery, the clip supply channel linked to the actuating rod for movement through rearward to forward excursion, the supply channel having a series of openings forming part of clip indexing means, the clip supply channel having a movable clip stop, a staple advancing mechanism positioned in the clip supply channel having upper and lower pawls cooperating respectively with the cover ratchet tooth surface and the supply channel series of openings and cooperating with the clip stop to advance the line of clips one step along the supply channel for each rearward to forward excursion of the actuating rod, means for separating a clip from the line of clips for each rearward to forward excursion of the actuating rod, means to move a clip into the jaws for each rearward to forward excursion of the actuating rod, and means for closing the jaws to apply a clip and to reopen the jaws for each rearward to forward excursion of the actuating rod.

13. A surgical clip applicator comprising manual operating means to provide reciprocating motion defined by a linear rearward to forward excursion for each cycle of the manual means, a stationary housing including a cover and base, the base being an elongate open ended channel connected at one of its ends to the manual operating means, clip applying jaws fitted to and extending from the other end of the base, the cover mounted to the base and together with the base defining stationary means for enclosing a clip actuating mechanism, the cover having first clip indexing means, a clip actuating means located within the housing and including an actuating rod for receiving reciprocating motion from the manual operating means, a clip supply channel for carrying a line of clips for application in surgery, the clip supply channel linked to the actuating rod for movement through rearward to forward excursion, the supply channel having second clip indexing means, means cooperating with the clip supply channel and with the first and second clip indexing means to advance the line of clips one step along the supply channel for each rearward to forward excursion of the actuating rod, a capture spring affixed to the cover for separating a clip from the line of clips for each rearward to forward excursion of the actuating rod, a pusher plate integral with the supply channel to move a clip into the jaws for each rearward to forward excursion of the actuating rod, and cam means forming part of the actuating rod for closing the jaws to apply a clip and to reopen the jaws for each rearward to forward excursion of the actuating rod.

14. A surgical clip applicator comprising a scissors-type handle for an inward and outward manual cycle to provide a linear rearward to forward excursion for each cycle, a stationary housing including a cover and base, the base being an elongate open ended channel connected at one of its ends to the handle, clip applying jaws fitted to and extending from the other end of the base, the cover mounted to the base and together with the base defining stationary means for enclosing a clip actuating mechanism, the cover having an inner surface with ratchet teeth having a pitch sufficient to index a clip one clip length along the actuating mechanism, clip actuating means located within the housing and including an actuating rod connected to the handle for receiving rearward and forward motion from the handle, a clip supply channel for carrying a line of clips for application in surgery, a movable clip stop spring formed integral with the supply channel for stopping the first of the line of clips, the clip supply channel attached to the actuating rod for movement through rearward to forward excursion, the supply channel having indexing openings with the same pitch as the ratchet teeth, clip advancing means fitted into the supply channel and having a spring head in engagement with the last of the line of clips, the clip advancing means further having a ratchet head with pawls in engagement with the cover ratchet teeth and the supply channel indexing openings, the clip advancing means cooperating with the cover ratchet teeth and the clip supply channel indexing openings, and with the clip stop spring to advance the line of clips one step along the supply channel for each rearward to forward excursion of the actuating rod, a capture spring mounted on the housing cover for separating a the first clip from the line of clips for each rearward to forward excursion of the actuating rod, a pusher plate integral with the supply channel for moving a clip into the jaws for each rearward to forward excursion of the actuating rod, cam means on the actuating rod for closing the jaws to apply a clip and to reopen the jaws for each rearward to forward excursion of the actuating rod.

15. A disposable surgical clip cartridge for use with manual operating means which provides the cartridge with linear reciprocating motion defined by a rearward to forward excursion, the cartridge comprising a stationary housing including a base and cover, the housing base being an elongate channel having an open end, clip applying jaws mounted at the open end of the base, the jaws being adapted to close in applying a clip and to open for receiving a clip, actuator means supported by the housing base for receiving rearward and forward strokes from the manual operating means, the actuator means for closing and opening the jaws, a clip channel for supplying a line of clips, the clip channel being affixed to the actuator means for reciprocating motion therewith, means for urging a line of clips through the supply channel, means for capturing the lead clip from the supply channel in response to motion of the actuator means and supply channel, and means for moving the lead clip into the applicator jaws.

16. A repeating surgical clip applicator comprising clip applicator jaws, means for generating reciprocal motion, a supply channel for holding a contiguous line of surgical clips being connected to said reciprocal motion generating means, biasing means for applying a force on the line of clips held in the supply channel, said biasing means being adapted to yield as the supply channel undergoes reciprocal motion, the supply channel having an integral clip stop spring cooperating with said biasing means to maintain the line of clips in contiguous condition as the supply channel undergoes reciprocal motion, means for releasing the clip stop spring and means for separating a lead clip from the contiguous line as the supply channel undergoes reciprocal motion, and the supply channel having an integral pusher plate for advancing a separated clip into the applicator jaws as the supply channel undergoes reciprocal motion.

17. A disposable surgical clip cartridge for use with manual operating means which provides linear reciprocating motion defined by a rearward to forward excursion, the cartridge comprising a stationary housing affixed to the manual operating means, an applicator mechanism located within the housing, the applicator mechanism having jaws for applying clips in surgery, a clip supply channel having a line of clips, the clip supply channel linked to the manual operating means for linear rearward to forward motion, means for urging the clips through the supply channel, means for applying a clip in surgery in response to rearward movement, means for separating a clip from the line on rearward movement of the clip supply channel, and means for loading a clip into the jaws in response to forward movement of the clip supply channel.

* * * * *